(12) United States Patent
Shimizu et al.

(10) Patent No.: US 6,632,497 B2
(45) Date of Patent: Oct. 14, 2003

(54) HOLLOW FIBROUS ORGANIC NANOTUBE AND METHOD FOR PRODUCING THE SAME

(75) Inventors: Toshimi Shimizu, Tsukuba (JP); George John, Tsukuba (JP); Mitsutoshi Masuda, Tokyo (JP)

(73) Assignee: National Institute of Advanced Industrial Science and Technology, Tokyo-to (JP)

( * ) Notice: Subject to any disclaimer, the term of this patent is extended or adjusted under 35 U.S.C. 154(b) by 129 days.

(21) Appl. No.: 09/939,841

(22) Filed: Aug. 28, 2001

(65) Prior Publication Data

US 2002/0051881 A1 May 2, 2002

(30) Foreign Application Priority Data

Sep. 7, 2000 (JP) ......................................... 2000-271192

(51) Int. Cl.⁷ .......................... B29C 35/16; B29C 67/06; B29C 67/24
(52) U.S. Cl. ........................ 428/36.9; 536/124; 536/126
(58) Field of Search .................... 428/36.9; 536/124, 536/126

(56) References Cited

U.S. PATENT DOCUMENTS 5,705,635 A * 1/1998 Shimizu et al. ............. 536/124

OTHER PUBLICATIONS

Patent Abstracts of Japan, vol. 2000, No. 10, Nov. 17, 2000—Abstract of JP 2000–204030.
Database WPI, Section Ch., Week 199419, Derwent Publications Ltd., London, GB; Class B03, AN 1994–132035 XP002184710—Abstract of JP 06–080685.

* cited by examiner

Primary Examiner—Sandra M. Nolan
(74) Attorney, Agent, or Firm—Wenderoth, Lind & Ponack, L.L.P.

(57) ABSTRACT

The invention provides a novel hollow fibrous organic nanotube comprising an O-glycoside type glycolipid having an aldose residue as the glycosyl group and a group represented by the general formula:

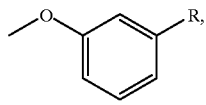

wherein R is an unsaturated straight-chain hydrocarbon group having 12 to 18 carbon atoms, as the aglycon. The nanotube structure can be obtained by gradually cooling a saturated aqueous solution of the starting material down to room temperature where the solution is kept standing for days or for weeks to cause spontaneous formation of hollow tubes as precipitates.

4 Claims, 1 Drawing Sheet

HOLLOW FIBROUS ORGANIC NANOTUBE AND METHOD FOR PRODUCING THE SAME

BACKGROUND OF THE INVENTION

The present invention relates to an organic nanotube which has a hollow fibrous form with an inner pore diameter of 10 to 20 nm, an outer diameter of 40 to 80 nm and a length of several tens μm to several hundreds μm, and which finds usefulness in the industries of fine chemicals, medicines and cosmetic and toiletry preparations as well as in the electronic information technology, energy industry and chemical industry, and also relates to a method for the preparation thereof.

A lipid of certain types self-assembles to form a stable molecular aggregate and is utilized as a functional material in fine chemical and medical fields. Such a lipid or, for example, the so-called ribosome which is a spherical aggregate comprising a phospholipid derived from a natural origin is produced by the thin film method, thermal dispersion method, solution injection method, cholic acid method or reverse layer method. These methods are all complicated and must use technologies requiring skillfulness. This offers difficulties in putting these methods into practice. Also, because molecular aggregates obtained by these methods all have a spherical morphology so that a hollow fibrous molecular aggregate having a large axial ratio, which is the ratio of the width to length of a fiber, cannot be obtained and consequently the application fields where these molecular aggregates are used are inevitably limited.

On the other hand, it is known that a fibrous or rod-shaped molecular aggregate is obtained by dispersing a synthetic amphiphilic compound in water ["Journal of American Chemical Society", Vol. 107, pages 509–510 (1985)].

However, although the molecular aggregate obtained by this method has a ribbon- or string-like fiber form, it is impossible to produce a nanotube structure having a unidimensional isolated void and a large surface area to be effective for gas storage and isolation of useful biomolecules and therefore has almost no utilizability as a fibrous molecular aggregate.

The present invention has been made with an object to provide a novel hollow fibrous organic nanotube which can be produced by a simple method from an inexpensive and renewable resource-based natural material of good availability along with regenerability and has a wide range of applicability.

SUMMARY OF THE INVENTION

The inventors of the present invention have repeatedly conducted extensive studies concerning a method of forming a functional material having a wide range of applicability simply from an easily available material and, as a result, found that an organic nanotube having a hollow fibrous structure can be obtained by causing molecular aggregation of an O-glycoside type glycolipid, in which the aglycon is a long-chain alkylphenol isolated from cashew nut shell liquid or a derivative thereof, by using several different methods and followed by quasi-crystallization of the glycolipid. Based on this finding, the present invention has been completed.

Accordingly, the present invention provides a hollow fibrous organic nanotube having an inner pore diameter of 10 to 20 nm and an outer diameter of 40 to 80 nm, the nanotube comprising an O-glycoside type glycolipid having an aldose residue as the glycosyl group and a group represented by the general formula:

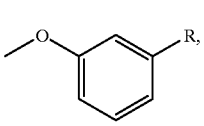
(I)

wherein R represents an unsaturated straight-chain hydrocarbon group having 12 to 18 carbon atoms, as the aglycon. The present invention also provides a process for producing the hollow fibrous organic nanotube having an inner pore diameter of 10 to 20 nm and an outer diameter of 40 to 80 nm, the process comprising the steps of dissolving the above O-glycoside type glycolipid in water at an elevated temperature to saturation, cooling the aqueous solution gradually and allowing the solution to stand at room temperature to cause spontaneous molecular aggregation and quasi-crystallization.

DETAILED DESCRIPTION OF THE PREFERRED EMBODIMENTS

Figure 1:
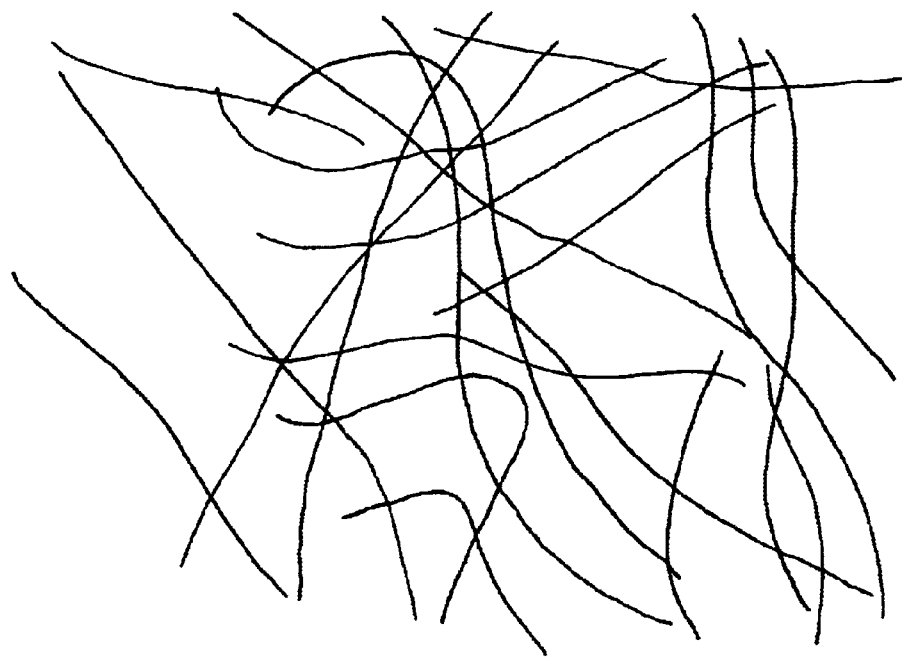
FIG. 1 is a sketch from an optical microscopic photograph of the organic nanotube obtained in Example 1.

The hollow fibrous organic nanotube according to the present invention is produced by using, as the starting material, an O-glycoside type glycolipid having an aldose residue as the glycosyl group and a long-chain alkylphenol residue represented by the above given general formula (I) as the aglycon or, namely, an O-glycoside type glycolipid represented by the general formula:

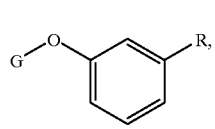
(II)

wherein R has the same meaning as above and G is an aldofuranose or aldopyranose residue in which the carbon atom at the reducing end participates in the O-glycoside bonding.

Examples of G in the aforementioned formula (II), i.e. the glycosyl group, include residues obtained by removing a hydrogen atom from a reducing end-hydroxyl group of an aldopyranose such as glucopyranose, galactopyranose, mannopyranose, allopyranose, altropyranose, gulopyranose, idopyranose and talopyranose as well as corresponding aldofuranoses.

Next, R in the above given formula (II) is an aliphatically unsaturated straight-chain hydrocarbon group having 12 to 18 or, preferably, 15 carbon atoms. Examples of such a hydrocarbon group include dodecyl group, tridecyl group, tetradecyl group, pentadecyl group, hexadecyl group, heptadecyl group and octadecyl group having a monoenic, dienic or trienic linkage introduced as an unsaturated structure. An 8-pentadecenyl group, 8,11-pentadecadienyl group and 8,11,14-pentadecatrienyl group are preferable in respect of good availability of source materials.

All of the O-glycoside type glycolipids represented by the aforementioned formula (II) are each a novel compound not described in any literatures.

Such an O-glycoside type glycolipid can be produced by reacting a (long-chain hydrocarbon group-substituted) phenol represented by the general formula:

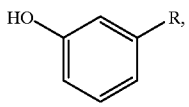
(III)

wherein R has the same meaning as above, with a reactive functional derivative of the reducing-end hydroxyl group of an aldopyranose or aldofuranose (hereinafter referred to simply as a protected aldose) in which all of the hydroxyl groups excepting that at the reducing end are protected, to form an O-glycoside bond and thereafter releasing the protective group. As the protective group, an acetyl group, benzyl group or 1,2-isopropylidene group is used.

Examples of the reactive functional derivative of the reducing-end hydroxyl group include trichloroacetoimidates, bromides (sugar bromides), fluorides (sugar fluorides), thioglycosides and O-acylates of the corresponding aldoses. Among these compounds, fluorides and trichloroacetoimidates react in a high yield and are therefore preferable.

Among the (long-chain hydrocarbon group-substituted) phenols represented by the general formula (III), those having an unsaturated straight-chain alkyl group having 15 carbon atoms can readily be obtained by using cashew nut shell liquid as the starting material. Namely, it is obtained by subjecting cashew nut shell liquid, which is commonly used as a starting material for cashew varnishes and brake pads and linings for machines or automobiles, to vacuum distillation to collect the cardanol fraction having a boiling point ranging from 220 to 235° C. The vacuum pressure in this vacuum distillation is preferably in the range from 250 to 700 Pa.

The cashew nut shell liquid is simply called cashew nut liquid and is an oily liquid obtained by processing a shell of a fruit of a cashew nut tree (*Anacardium occidentale*) belonging to the family of Anacardiaceae by solvent extraction or fractional distillation under heating. The cashew nut liquid is obtained as a mixture consisting mainly of anacardic acid and cardol in the case of processing by solvent extraction and as a mixture consisting mainly of cardanol and cardol in the case of processing by fractional distillation under heating.

Optionally, this cashew nut shell liquid is subjected to an extraction treatment with an organic solvent such as n-hexane to give cardanol which is dissolved in a solvent and used as the starting material in the present invention.

On the other hand, the reactive functional derivative of the protected aldose which is to be reacted with this long-chain alkylphenol may be produced in the following manner.

Thus, the halogenated product or sugar bromide or fluoride by bromination or fluorination at the reducing-end hydroxyl group of an aldose is obtained by acetylating the aldose in pyridine followed by a reaction with hydrogen bromide or hydrogen fluoride in acetic acid.

The corresponding trichloroacetoimidate is obtained by acetylation of the aldose in the same manner as above followed by the reaction with hydrazine acetate in dimethylformamide to give a sugar chain ingredient selectively deacetylated at the reducing end only which is then reacted with trichloroaceto-nitrile in the presence of a basic catalyst. The reaction solvent used here includes preferably halogen compounds such as methylene chloride and chloroform and the basic catalyst includes preferably sodium hydride and cesium carbonate.

In the reaction for obtaining the halide of the aldose, the α-isomer is selectively obtained. In the reaction for obtaining the trichloroacetoimidate, the α-isomer is selectively obtained if the reaction is continued for 2 hours or longer at room temperature. These facts can be evidenced by the $^1$H-NMR spectrum of each compound in d-chloroform at 25° C. showing a doublet signal (spin-spin coupling constant=3.4 to 4.0 Hz) at 6.4 to 6.6 ppm of the δ value.

Next, the reaction for forming the O-glycoside linkage from the long-chain alkylphenol represented by the general formula (III) and the reactive functional derivative of the protected aldose is performed in the following manner.

For example, when the reactive functional derivative of the protected aldose is a bromide, the reaction is performed in the presence of a basic material by using tin trifluoromethanesulfonate as a catalyst. As the reaction solvent in this case, chloroform or toluene is used but a chloroform/toluene mixture is preferable in respect of the solubility behavior. As the basic material, 2,4,6-trimethylpyridine or 1,1,3,3-tetramethylurea is used. In this case, the reaction temperature is from room temperature to 40° C. and the reaction is completed usually within 10 to 20 hours. A still higher yield of the product can be ensured by conducting the reaction in the presence of molecular sieve 4A.

When the reactive functional derivative of the protected aldose is trichloroacetoimidate, the reaction is performed in the presence of a Lewis acid catalyst. The reaction solvent used here is exemplified by halogenated solvents such as chloroform, methylene chloride and 1,2-dichloroethane, acetonitrile and nitromethane. Particularly, methylene chloride is preferable. The Lewis acid catalyst used in this reaction is trimethylsilyl trifluoromethanesulfonate or a boron trifluoride/ether complex. The amount of the Lewis acid catalyst to be used is preferably 2 to 3 equivalents relative to the amount of trichloroacetoimidate. In this case, the reaction temperature is selected in the range from −5 to 0° C. The reaction time is usually 2 to 3 hours, though dependent on the types of the Lewis acid and the reaction temperature. This reaction is preferably conducted in the presence of a molecular sieve under agitation.

If glucose is used as the aldose and a boron trifluoride/ether complex is used, the glucose can be converted directly to an aldose compound in which all of the hydroxyl groups including the reducing-end hydroxyl group are acetylated without conversion of the glucose in advance into trichloroacetoimidate so that the O-glycoside can be obtained in a high yield. This method is particularly advantageous when glucose is used in respect of the high yield of the reaction product.

When the bromide or trichloroacetoimidate is used, the β-isomeric O-glycoside is selectively obtained. This fact is evidenced from the $^1$H-NMR spectra (in dimethylsulfoxide-$d_6$ at 25° C.) of each of these compounds showing a doublet signal (spin-spin coupling constant=7.8 to 8.0 Hz) at 4.4 to 4.9 ppm of the δ value.

It is necessary to remove the protective groups finally from the O-glycoside type glycolipid containing the protected aldose residue and obtained in the above manner.

The reaction for removing the protective groups or, for example, acetyl groups can be performed by treating the O-glycoside having the protected sugar chain structure with an alkali metal alcoholate such as sodium methoxide and potassium methoxide followed by neutralization with a strongly acidic cation exchange resin. Alternatively, it is a simpler way that an aqueous solution of a trialkylamine such as trimethylamine is mixed with several times by volume of a reaction solvent and the reaction of the O-glycoside having the above mentioned protected sugar chain structure is conducted therein. In this case, the concentration of the aqueous trialkylamine solution is preferably in the range from 30 to 50% by weight. As the reaction solvent in this case, an alcoholic solvent such as methyl alcohol and ethyl alcohol or a mixed solvent of an ether solvent such as diethyl ether and tetrahydrofuran and an alcoholic solvent is used preferably. At this time, it is desirable that the pH of the reaction solution be kept at 8.0 to 8.5 in order to avoid certain side-reactions such as hydrolysis of the ester linkage. The reaction is completed usually within 12 to 24 hours though dependent on the reaction conditions. By distilling off the solvent from the reaction mixture after completion of the reaction, an O-glycoside type glycolipid having the long-chain alkylphenol residue represented by the aforementioned general formula (I) as the aglycon is obtained in the form of a white powder. The crude product obtained in this manner can be isolated and purified into a high purity product chromatographically by using a silica gel column.

A good coincidence can usually be obtained in the elementary composition of the O-glycoside type glycolipid between the actual analytical values with the product obtained in this manner and the calculated values for the same compound within analytical errors. Further, the compound having a sugar chain structure protected by acetyl groups can readily be identified from the $^1$H-NMR spectrum in d-chloroform at 25° C. exhibiting a characteristic signal assignable to the hydrogen atoms of the methyl groups of the acetyl groups at a δ value of 2.03 to 2.08 ppm.

On the other hand, the compound as the product from which the acetyl groups have been removed can be identified from the $^1$H-NMR spectrum in dimethylsulfoxide-$d_6$ at 25° C. exhibiting signals at the δ values of 0.88 ppm (hydrogen atoms of the methyl group of a long-chain alkyl group), 1.26 ppm (hydrogen atoms of the methylene group of the long-chain alkyl group), 1.58 ppm (hydrogen atoms of the second methylene group from the aromatic portion in the long-chain alkyl group), 2.56 ppm (hydrogen atoms of a methylene group directly bonded to the aromatic portion), 3.13–3.69 ppm (hydrogen atoms bonded to C2, C3, C4, C5 and C6 carbon atoms of the sugar chain), 4.82 ppm (anomeric hydrogen atoms bonded to the C1 carbon atom of the sugar chain), 5.34–5.42 ppm (hydrogen atoms bonded to the vinyl group) and 6.79, 6.80–6.89 ppm, 7.19–7.20 ppm (hydrogen atoms bonded to the aromatic ring).

Next, the O-glycoside type glycolipid obtained in this manner is used to produce a hollow fibrous organic nanotube in the following manner. First, water is added to the O-glycoside as the starting material and the mixture is heated to prepare a saturated aqueous solution. In this case, when the amount of water is too small, a portion of the solute remains undissolved whereas, when the amount of water is too large, the concentration does not reach saturation. Therefore, the amount of water is selected in the range from 20 to 1000 times that of the O-glycoside by weight. In this case, the heating temperature is preferably raised up to the boiling point in order to increase the amount of the dissolved O-glycoside as high as possible. However, it is optional that the temperature is lower than the boiling point.

Next, the saturated aqueous O-glycoside solution prepared in this manner is gradually cooled and kept standing at room temperature to cause spontaneous formation of a hollow fibrous organic nanotube therein. At this time, if the cooling rate is too large, a fiber of a large length can hardly be formed and aggregates of short fibers are produced. It is preferable that the cooling rate be selected in the range not exceeding 0.5° C./minute or, in particular, not exceeding 0.2° C./minute. While the solvent used in the preparation of the aqueous solution is usually water alone, it is optional, if desired, to use a mixture of water and an alcohol. As the alcohol in this case, for example, a water-miscible alcohol such as methyl, ethyl and propyl alcohols can be used.

After lapse of 1 to 2 days following gradual cooling in this manner, precipitation of a fibrous material proceeds in the aqueous solution. Almost all of the fibers obtained by aging for several days in this manner, however, have a morphology in which a ribbon fiber is wound up coil-wise in the direction of the longer axis according to the observation by using a polarizing microscope or phase-contrast microscope. In order to obtain a hollow fibrous nanotube, it is necessary for the solution to be kept standing at room temperature for further 2 to 3 weeks with the fibrous material left in the aqueous solution. In order to convert all of the fibers from the coil-like form to a complete tube-like structure, it is desirable to allow the aqueous solution to be kept standing for about one month as an aging period and this is desirable for increasing the yield of the organic nanotubes. The fibers obtained in this manner are collected and air-dried or vacuum-dried to obtain a hollow fibrous organic nanotube which is stable in air and has an inner diameter of the pore of 10 to 20 nm, outer diameter of 40 to 80 nm and length of several tens μm to several hundreds μm.

The form of the resulting tube-like structure can easily be observed using a standard optical microscope. The tube structure can be recognized to further detail by using a laser microscope, atomic force microscope or electron microscope.

The hollow fibrous organic nanotube obtained by the process of the present invention can be utilized, for example, as a clathrate and separating material and drug delivery material for a medicament and useful biomolecules in the fields of fine chemical industries, pharmaceutics and cosmetic preparations or as a microelectronic part in the electronic and information technologies by coating the nanotube with a conductive material or a metal. Further, the hollow fibrous organic nanotube is useful as a gas storage material in the energy industry and also as an artificial blood vessel, nanotube capillary and nanoreactor which utilizes the fine tubular structure in the fields of medical treatment, analysis and chemical product manufacturing, exhibiting high industrial usefulness.

In the following, the present invention will be described in more detail by way of examples, which, however, never limit the scope of the present invention.

As to the Rf value of the thin-layer chromatography, the value obtained when a 6:4 by volume mixture of hexane and ethyl acetate was used as the developing solvent was recorded as $Rf_1$.

Reference Example 1

Cashew nut shell liquid (CNSL) was subjected twice to vacuum distillation under a pressure of about 400 Pa to collect the fraction having a boiling point of 220 to 230° C. thereby obtaining cardanol. A 1.52 g (5 mmoles) portion of the thus obtained cardanol was dissolved in 10 ml of dehydrated methylene chloride and 1.95 g (5 mmoles) of β-D-glucose pentaacetate and 0.62 ml (5 mmoles) of boron trifluoride diethyl ether were added thereto in the presence of 2 g of molecular sieve 4A. After the reaction mixture was stirred for 24 hours at room temperature, the reaction mixture was poured into an aqueous 5%-sodium hydrogencarbonate solution. The organic phase was separated by phase separation and washed with an aqueous sodium hydrogencarbonate solution and then with water followed by drying on anhydrous sodium sulfate. The organic solvent was completely distilled off under reduced pressure and the resulting crude product was recrystallized from ethanol. The resulting solid product was subjected to column chromatography using, as the eluent, a 7:3 by volume mixture of hexane and ethyl acetate to obtain 2.36 g (yield: 75%) of 1-(O-β-D-glucopyranosidotetraacetate) cardanol as a white solid.

The physical properties of the resulting product are as follows.

Rf value: $Rf_1$=0.47 in the thin-layer chromatography
Melting point: 60° C. Elementary analysis value $(C_{35}H_{50}O_{10})$

|  | C | H |
| --- | --- | --- |
| Calculated (%) | 66.65 | 7.99 |
| Found (%) | 66.78 | 7.82 |

Next, 1.26 g (2 mmoles) of the 1-(O-β-D-glucopyranosidotetraacetate) cardanol were added to a 1:4 by volume mixture of a 45% by weight aqueous solution of trimethylamine and methyl alcohol to effect the reaction for 24 hours. The solvent was removed by distillation under reduced pressure and then the resulting syrupy residue was crystallized from a methyl alcohol/acetonitrile (volume ratio=1:2) mixed solvent and recrystallized from the same solvent to obtain 0.88 g (yield: 95%) of the desired deacetylated 1-(O-β-D-glucopyranoside) cardanol almost quantitatively as a white solid.

The physical properties of the resulting product are as follows.

Melting point: 135.2° C. Elementary analysis value $(C_{27}H_{42}O_6)$

|  | C | H |
| --- | --- | --- |
| Calculated (%) | 70.10 | 9.15 |
| Found (%) | 70.39 | 9.44 |

EXAMPLE 1

Figure 2:
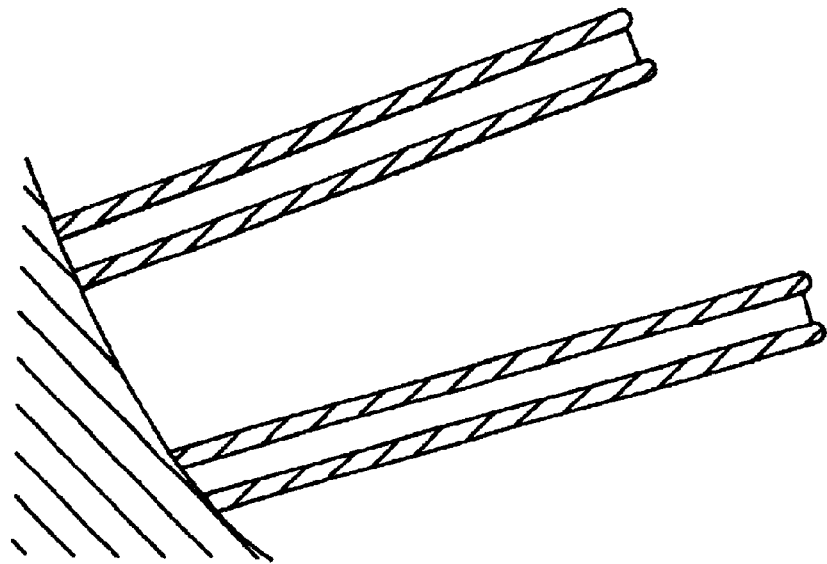
FIG. 2 is a sketch from a transmission electron microscopic photograph of the organic nanotube obtained in Example 1.

A 5 mg portion of 1-(O-β-D-glucopyranoside) cardanol obtained in Reference Example 1 was taken and placed in a flask. To this were added 100 ml of water and the mixture was heated using a mantle heater to effect boiling and dissolving. The heating temperature of the mantle heater was gradually decreased under control down to room temperature at a cooling rate of 0.2° C./minute and the mixture was then kept standing at room temperature for one month. A small portion of the resulting aqueous mixture containing fibrous materials was taken and inspected under an optical microscope to find a fibrous structure with a length of several tens μm to several hundreds μm. Further, when the resulting product was evaluated by observation using a transmission electron microscope and, as a result, a hollow fibrous organic nanotube material having an inner pore diameter of about 10 to 15 nm and an outer diameter of about 40 to 50 nm was detected. FIGS. 1 and 2 are each a sketch from an optical microphotograph of the resulting organic nanotubes and a transmission electron microscopic photograph thereof, respectively.

EXAMPLE 2

A hollow fibrous organic nanotube was obtained in the same manner as in Example 1 except that a 10:1 by volume water/ethanol mixture was used as the solvent and heated to about 70° C. in place of the boiling water in Example 1. The resulting organic nanotube was found to have a hollow fibrous structure with an inner pore diameter of about 10 to 20 nm, an outer diameter of about 40 to 60 nm and a length of several tens μm to several hundreds μm as inspected by using a transmission electron microscope.

EXAMPLE 3

A hollow fibrous organic nanotube was obtained in the same manner as in Example 1 except that a 10:1 by volume water/acetone mixture was used as the solvent and heated to about 70° C. in place of the boiling water in Example 1. The resulting organic nanotube was found to have a hollow fibrous structure with an inner pore diameter of about 10 to 20 nm, an outer diameter of about 40 to 60 nm and a length of several tens μm to several hundreds μm as inspected by using a transmission electron microscope.

What is claimed is:

1. A hollow fibrous organic nanotube having an inner pore diameter of 10 to 20 nm and an outer diameter of 40 to 80 nm and consisting of an O-glycoside-based glycolipid having an aldose residue as the glycosyl group and a group represented by the general formula:

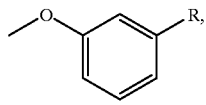

wherein R is an unsaturated straight-chain hydrocarbon group having 12 to 18 carbon atoms, as the aglycon.

2. A method for the preparation of a hollow fibrous organic nanotube having an inner pore diameter of 10 to 20 nm and an outer diameter of 40 to 80 nm as defined in claim 1 which comprises the steps of:

(a) dissolving an O-glycoside-based glycolipid compound having an aldose residue as the glycosyl group and a group represented by the general formula:

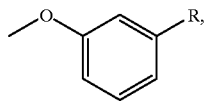

wherein R is an unsaturated straight-chain hydrocarbon group having 12 to 18 carbon atoms, as the aglycon, in water at an elevated temperature to form a saturated aqueous solution thereof;

(b) gradually cooling the saturated aqueous solution down to room temperature; and (c) allowing the solution to be kept standing at room temperature to cause spontaneous molecular aggregation and quasi-crystallization of the glycolipid compound.

3. The method as claimed in claim 2 in which the elevated temperature in step (a) is the boiling point of the solution.

4. The method as claimed in claim 2 in which the cooling rate of the mixture in step (b) does not exceed 0.5° C./minute.

* * * * *